United States Patent [19]

Jentsch et al.

[11] Patent Number: 5,414,104
[45] Date of Patent: May 9, 1995

[54] PROCESS FOR PREPARING DIALKYL CARBONATES

[75] Inventors: Joerg-Dietrich Jentsch, Mülheim; Alexander Klausener, Köln; Heinz Landscheidt, Duisburg; Erich Wolters, Köln; Eberhard Zirngiebl, Köln, all of Germany

[73] Assignee: Bayer Aktiengesellschaft, Leverkusen, Germany

[21] Appl. No.: 231,607

[22] Filed: Apr. 22, 1994

[30] Foreign Application Priority Data

Apr. 29, 1993 [DE] Germany .................. 43 14 038.6

[51] Int. Cl.⁶ .................................. C07C 69/96
[52] U.S. Cl. .................................. 558/277
[58] Field of Search ........................ 558/277

[56] References Cited

U.S. PATENT DOCUMENTS 5,231,213  7/1993  Landscheidt et al. .

FOREIGN PATENT DOCUMENTS 0425197  5/1991  European Pat. Off. .
0501507  9/1992  European Pat. Off. .
0503091  9/1992  European Pat. Off. .
0503618  9/1992  European Pat. Off. .
0559001  9/1993  European Pat. Off. .
4123603  1/1993  Germany .

OTHER PUBLICATIONS

Chinese Science Bulletin, vol. 34, No. 10, May 1989; "A New Way for Catalytic Synthesis of Dimethyl Carbonate", Z. Yong-bao et al.; page of contents+pp. 875–876.
Zeitschrift für katalytische forschung vol. 10, No. 1, Mar. 1989, pp. 1–13 (Journal of Catalytic Research [China]); "Erforschung einer neuen methode der katalytischen . . . ", J. Xuan-zhen et al.

Primary Examiner—Mary C. Lee
Assistant Examiner—Michael G. Ambrose
Attorney, Agent, or Firm—Sprung Horn Kramer & Woods

[57] ABSTRACT

Dialkyl carbonates can be prepared by reaction of carbon monoxide with alkyl nitrites in a continuous gas-phase reaction using a platinum metal catalyst on a metal phosphate support and adding hydrogen halide stepwise or continuously during the course of the reaction in almost quantitative selectivity; the corresponding dialkyl oxalates are formed in such small amounts that in most cases they cannot be detected.

20 Claims, No Drawings

PROCESS FOR PREPARING DIALKYL CARBONATES

BACKGROUND OF THE INVENTION

1. Field of the Invention

The present invention relates to a process for preparing dialkyl carbonates by reaction of carbon monoxide (CO) with alkyl nitrites in the presence of a catalyst selected from the group consisting of platinum metal halides on a support of metal phosphate having acid centres.

Dialkyl carbonates are of general chemical importance. For instance, diethyl carbonate is an excellent solvent in the middle boiling-point range. Furthermore, dialkyl carbonates are excellent carbonylation and acylation reagents. Finally, they have great importance in the preparation of other carbonates, of urethanes and of ureas.

2. Description of the Related Art

It is known that dialkyl carbonates can be prepared by reactions of phosgene or of alkyl chloroformates with alcohols. However, there is increasing interest in avoiding the use of the toxic phosgene or the intermediates derived therefrom, such as the chloroformic esters, by means of other processes. Besides attempts to obtain dialkyl carbonates by reaction of CO with lower alcohols, processes in which CO is reacted in the gas phase with alkyl nitrite over a platinum metal catalyst are of particular importance. In such reactions, the formation of dialkyl oxalate in addition to the desired dialkyl carbonate is frequently observed.

Thus, the Journal for Catalytic Research (China), Volume 10(1), pp. 75–78, describes the reaction of CO and methyl nitrite over a $PdCl_2$-containing activated-carbon catalyst, which in addition to dimethyl oxalate gives mostly dimethyl carbonate.

A Pd/carbon catalyst for the preparation of dimethyl carbonate from CO and methyl nitrite is also described in Chin. Sci. Bull. 34 (1989), 875–76.

Furthermore, EP 425 197 discloses a process which in its preferred embodiment gives dialkyl carbonates of methanol or ethanol from CO and methyl or ethyl nitrite in the gas phase over a $PdCl_2$ catalyst on activated carbon. According to said EP 425 197, Table 1, the selectivities in respect of the desired lower dialkyl carbonates reach values of up to 94%, but lower dialkyl oxalates and $CO_2$ are always observed as by-products. Furthermore, the reported high selectivities were not satisfactorily reproducible when the work was repeated. The catalysts of this EP 425 197 contain additions of chlorides of base metals; a considerable amount of hydrogen chloride, namely an amount from 1 to 50 mol%, based on the platinum metal in the catalyst, is added to the system, or part of the catalyst has to be taken from the reactor and subjected to treatment with hydrogen chloride.

EP 501 507 describes the use of zeolites as support material. This does avoid some of the abovedescribed disadvantages, but at the same time a significant deterioration occurs in the selectivity in respect of the methyl nitrite used. Thus, according to Example 1, only a selectivity of 79%, based on methyl nitrite, is achieved.

In EP 503 091 and EP 503 618, the properties of the catalysts based on activated carbon are improved by further additions, for example, of copper and molybdenum or copper, molybdenum and potassium fluoride. But here too there occurs a decrease in catalyst activity, which in an industrial process leads to appreciable extra cost. These resulting disadvantages caused, such as increased need for regulation due to changing (falling) conversions and downtimes during replacement of the deactivated catalyst, are particularly noticeable in a cycle process in which the NO formed in the reaction is recirculated and converted into methyl nitrite. Also disadvantageous are the low conversions of methyl nitrite which are achieved. This is likewise disadvantageous in connection with the abovementioned cycle gas process.

In DE-OS (German Published Specification) 41 23 603, a high selectivity, based on both CO and methyl nitrite, with simultaneously high conversion is achieved by use of a palladium chloride catalyst with $\gamma$-$Al_2O_3$ as support material. However, maintenance of the catalytic activity requires the addition to the starting mixture of hydrogen chloride gas in amounts of up to 1000 ppm. This can lead to corrosion problems.

SUMMARY OF THE INVENTION

It has now been found that the disadvantages described can be overcome by the use of supported platinum metal catalysts whose supports are metal phosphates having acid centres. According to the invention, metal phosphates are used as tablets or binder-containing extrudates. Suitable binders are, for example, $SiO_2$, $Al_2O_3$ or clay minerals. The binder contents can be varied within a wide range, for example from 0.5 to 99.5% by weight, based on the total weight of the support.

A process has been found for preparing dialkyl carbonates of the formula $$O=C(OR)_2 \qquad (I),$$

in which

R represents a straight-chain or branched $C_1$–$C_4$-alkyl, by reaction of carbon monoxide (CO) with alkyl nitrites of the formula $$RONO \qquad (II)$$

in which

R is as defined above, in the presence or absence of an inert gas and also in the presence or absence of the alcohol ROH on which it is based and also in the presence or absence of NO over a supported platinum metal catalyst at elevated temperature in a continuous gas-phase reaction, which is characterized in that metal phosphates having acid centres are used as support, the platinum metal is present in the form of a halide or a halide-containing complex, which may each be formed in situ in the process reactor from the platinum metal or a halogen-free platinum metal compound with the aid of hydrogen halide under the reaction conditions, the reaction is carried out with a volume ratio of nitrite: CO=0.1–10:1, a pressure from 0.5 to 6 bar and a temperature from 50° to 150° C., and hydrogen halide is added stepwise or continuously.

DETAILED DESCRIPTION OF THE INVENTION

The following metal phosphates, inter alia, are suitable for use as catalyst supports according to the invention: Acid metal phosphates including acid metal monohydrogen phosphates and acid metal dihydrogen phosphates of elements of Group II A, Group III A, Group III B, Group IV B and Group V B of the Periodic Table of the Elements (Mendeleev), rare-earth metals of atomic numbers 58–71 and of the actinides having atomic numbers 89–92, both as chemically uniform pure substances and as mixtures. Preferably these are one or more metal phosphates, metal monohydrogen phosphates or metal dihydrogen phosphates selected from the group consisting of magnesium, calcium, strontium, barium, titanium, zirconium, hafnium, vanadium, niobium, tantalum, boron, aluminium, gallium, indium, lanthanum, cerium, praseodymium, neodymium, samarium, europium, gadolinium, terbium, dysprosium, holmium, erbium, thulium, ytterbium, lutetium and uranium.

Catalyst supports used according to the invention can be produced by precipitation of the desired acid metal phosphate, hydrogen phosphate or dihydrogen phosphate, washing of the precipitate to remove inorganic by-products and drying.

Dried catalyst supports can, if desired, be further modified by extruding, tabletting, admixing of further catalyst supports such as $Al_2O_3$ or $SiO_2$ and calcining.

Preparation and further processing are well known to those skilled in the art and are state of the art.

Use of the above-described preparative methods gives porous solids which contain Lewis and Brönstedt acid centres and are insoluble in the reaction medium. Their composition varies because of dependence on many preparation conditions, such as temperature, concentration and nature of the reactants, rate and order of introduction of the reactants, pH during the preparation, duration of the precipitation, volume and pH of the wash solutions, duration and temperature of drying and calcination, etc. However, this changing composition of the phosphates little affects their suitability as catalyst supports.

The acid phosphates, hydrogen phosphates and dihydrogen phosphates- of aluminium, vanadium, niobium, yttrium, lanthanum, the rare-earth metals (atomic numbers 58–71) and mixtures thereof have proven particularly suitable.

The advantages achieved by use of the catalyst support of the invention can optionally be further improved by addition of a compound of iron, copper, bismuth, cobalt, nickel, tin, molybdenum, tungsten and of alkali and alkaline-earth metals or a mixture of a plurality thereof.

The reaction in the process of the invention proceeds according to the following reaction equation:

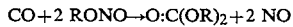

$$CO + 2\ RONO \rightarrow O{:}C(OR)_2 + 2\ NO$$

R is here a straight-chain or branched alkyl having 1–4 carbon atoms, for example methyl, ethyl, propyl, isopropyl, butyl, isobutyl, preferably methyl and ethyl and particularly preferably methyl.

In principle it is possible to start from a mixture of various alkyl nitrites, but this results in a mixture of various dialkyl carbonates with or without as symmetrically substituted dialkyl carbonates. In the interests of a uniform reaction, it is therefore preferred that only one alkyl nitrite be used as starting material.

Although it is possible in principle to react CO with an alkyl nitrite without any further components in the mixture, for example if the composition of the mixture is outside the explosive limits, an inert gas is often introduced for dilution of the reactants. Examples of inert gases are noble gases, nitrogen and carbon dioxide, preferably argon, nitrogen or carbon dioxide, particularly preferably nitrogen and carbon dioxide. The amount of inert gas is from 20 to 80% by volume, preferably from 30 to 70% by volume, based on the total gas volume to be introduced into the reactor. The inert gas and any unconverted residual amounts of reactants contained therein can be recirculated.

The volume ratio of the reactants nitrite and CO to one another is from 0.1 to 10:1, preferably from 0.2 to 4:1, particularly preferably from 0.3 to 3:1.

The gas mixture to be reacted can further contain small amounts of alcohol ROH, for example in an amount from 0 to 10% by volume, and small amounts of NO, for example in an amount from 0 to 10% by volume, each based on the total volume of the gas mixture to be used. Such additions of ROH or NO can originate, for instance, in the preparation of the alkyl nitrite and can, for example, be carried with it into the reaction gas mixture.

The catalyst for the process of the invention is applied to metal phosphates as support. In the active state, its reactive component comprises a platinum metal halide or a complex compound containing platinum metal halide. Such complex compounds are basically known and are, for example, alkali metal chloride complex compounds, such as lithium or sodium tetrachloropalladate, $Li_2[PdCl_4]$ or $Na_2[PdCl_4]$.

It has furthermore been found, that the platinum metal halide or the complex containing the platinum metal halide can be formed in situ in the reactor from metallic platinum metal or a halogen-free platinum metal compound under the reaction conditions, i.e. in the presence of the gas mixture to be reacted, with the aid of hydrogen halide. Accordingly, the reactor can also be filled with an otherwise comparable catalyst which initially contains the platinum metal in metallic form or has been prepared with the aid of a halogen-free platinum metal compound. Examples of such halogen-free platinum metal compounds which are suitable for this purpose are platinum metal nitrates, propionates, butyrates, carbonates, oxides, hydroxides or others which are familiar to those skilled in the art.

Elements of the platinum metal group for the purposes of the invention are palladium, platinum, iridium, ruthenium and rhodium, preferably palladium, ruthenium and rhodium, particularly preferably palladium.

Halides for the purposes of the invention are fluoride, chloride, bromide and iodide, preferably chloride and bromide, particularly preferably chloride.

The amount of platinum metal halide or of the complex containing the platinum metal halide in the active state is from 0.01 to 8% by weight, preferably from 0.05 to 4% by weight, calculated as platinum metal and based on the total weight of the catalyst.

The preparation of a catalyst to be used according to the invention is carried out by methods which are basically known to those skilled in the art. Thus, the support can be impregnated or sprayed with a solution of one or more of the specified platinum metal compounds. The specified addition(s) is/are carried out in the same way. In the case where the platinum metal is to be immobilized on the support in the form of the metal, carbonate, oxide or hydroxide and not activated to the platinum metal halide in the described manner with the aid of hydrogen halide under reaction conditions until in the reactor, the platinum metal compound applied can, in a manner known to those skilled in the art, be reduced to the metal by means of a suitable reducing agent or be converted to the carbonate, oxide or hydroxide by means of a suitable precipitant.

Furthermore, it has been observed that to achieve uniformly high selectivities for dialkyl carbonate it is advantageous to allow hydrogen halide to act on the catalyst during its time on stream. In fact, it was basically found that the yield rises with the amount of hydrogen halide. Thus, the concentration of hydrogen halide (e.g. HCl) which is brought into contact with the catalyst with the feed material can be, for example, up to 1000 ppm. However, it has further been observed that this amount of hydrogen halide can be significantly smaller. It is thus merely necessary to replace the amount of hydrogen halide from the activated form of the catalyst which is carried away with the reaction products. This amount can be determined by analysis. It generally varies within a range from 1 to 2000 μg of hydrogen halide per g of dialkyl carbonate formed. For ease of workup, it may be desirable to use a small amount of hydrogen halide.

Hydrogen halide for the purposes of the invention is hydrogen fluoride, hydrogen chloride, hydrogen bromide and hydrogen iodide, preferably hydrogen chloride and hydrogen bromide, particularly preferably hydrogen chloride.

The hydrogen halide can be metered as such in gaseous form into the reaction mixture. However, it can also be metered as a solution in one of the materials present in the reaction mixture, for example dissolved in the alcohol on which the alkyl nitrite is based.

The specified catalysts can be used at a gas hourly space velocity (GHSV) from 700 to 5000 l of the mixture of the gaseous reactants per l of catalyst per hour.

The process of the invention is carried out at a temperature from 50° to 150° C., preferably from 70° to 120° C., particularly preferably from 70° to 110° C., and at a pressure from 0.5 to 10 bar, preferably 0.8–7 bar, particularly preferably from 1 to 6 bar, most preferably from 1 to 5 bar.

The preparation of the alkyl nitrites to be used according to the invention is carried out according to known processes, for example from the appropriate alcohol and nitrous acid which is, for instance, formed in situ from an alkali metal nitrite and a mineral acid, such as sulphuric acid. The nitrogen monoxide NO formed during the course of the process of the invention can be continuously regenerated with oxygen and fresh alcohol to give alkyl nitrite (DE-OS [German Published Specification] 38 34 065) and recirculated together with unconverted reactants.

EXAMPLES

Definitions

The space time yield (STY) in [g/l.h] and for dimethyl carbonate in the examples is calculated according to:

$$\frac{m_{DMC}}{V_{cat} \cdot t},$$

where $m_{DMC}$ is the mass of dimethyl carbonate (DMC) formed,
$V_{cat}$ is the catalyst volume and t is the time.
The selectivity S (%) is calculated according to:

$$S = \frac{n_{DMC}}{n_{DMC} + 2 \times n_{DMO} + n_{MF} + n_{FDA}} \times 100[\%]$$

where
$n_{DMC}$ = number of moles of dimethyl carbonate
$n_{DMO}$ = number of moles of dimethyl oxalate
$n_{MF}$ = number of moles of methyl formate
$n_{FDA}$ = number of moles of formaldehyde dimethylacetal.

Example 1

(Preparation of a catalyst)

2.25 l of a solution containing 396 g (3 mol) of ammonium hydrogen phosphate were added dropwise to a solution of 650 g (1.5 mol) of lanthanumnitrate hexahydrate in 4.5 l of deionized water at +50° C. over a period of 60 minutes. The pH of the white suspension obtained was adjusted to 6 with aqueous ammonia. The mixture was stirred for a further 30 minutes and the product was filtered off with suction and washed free of nitrate on the suction filter. After 18 hours' drying at 120° C. the material was calcined at 500° C. (16 h) and tabletted.

100 ml of the catalyst support thus obtained were impregnated with an aqueous $Li_2PdCl_4$ solution and the product was dried at 80° C. in vacuo (29 torr). The catalyst then contained 8 g of Pd/l.

Example 2

(Preparation of a catalyst)

3 l of dilute phosphoric acid, corresponding to 408 g = 4.16 mol of 100% strength phosphoric acid, were added dropwise to a solution of 900 g (2.1 mol) of lanthanum nitrate hexahydrate in 3 l of deionized water at 50° C. over a period of 15 minutes. The suspension was adjusted to pH=6 with aqueous ammonia and stirred for a further 3 hours at 50° C.

After washing on the suction filter the product was dried for 12 h at 120° C. and tabletted.

100 ml of the catalyst support thus obtained were impregnated with an aqueous $Li_2PdCl_4$ solution and the product was dried at 80° C. in vacuo (29 torr). The catalyst then contained 8 g of Pd/l.

Example 3

(Illustration of the process)

In a vertical glass tube (length 50 cm, diameter 4 cm), 20 ml of the catalyst of Example 1 were introduced between a packing of Raschig rings.

The glass tube was heated to 90° C. and a gas mixture containing 55% of $N_2$, 20% of methyl nitrite (MeONO), 20% of CO and 5% of methanol (MeOH) was passed through. 50 ppm of HCl (by volume) were added to the gas mixture. The space velocity was 1000 l/l -h.

The gas flowing from the reactor was cooled to 5° C. and the condensed phase obtained analysed by gas chromatography.

The products which were not condensed were measured by IR spectroscopy and mass spectroscopy.

After 2 h, dimethyl carbonate was being formed at an STY of 140 g/l -h and S=99%.

Even after 10 h the STY was 140 g/l -h and S was 99%.

Example 4

Example 4 was carried out as in Example 3. 10 ml of the catalyst of Example 2 were used.

After 2 h dimethyl carbonate was being formed at an STY of 145 g/l -h and S=99%.

Even after 10 h the STY was 145 g/l -h and S was 99%.

What is claimed is:

1. A process for preparing a dialkyl carbonate of the formula $$O=C(OR)_2,$$

in which

R represents a straight-chain or branched $C_1$–$C_4$-alkyl, by reaction of carbon monoxide (CO) with an alkyl nitrite of the formula

RONO, in which

R is as defined above, in the presence or absence of an inert gas and also in the presence or absence of the alcohol ROH on which it is based and also in the presence or absence of NO over a supported platinum metal catalyst at elevated temperature in a continuous gas-phase reaction, wherein a metal phosphate having acid centres is used as support, the platinum metal is present in the form of a halide or a halide-containing complex, which may each be formed in situ in the process reactor from the platinum metal or a halogen-free platinum metal compound with the aid of hydrogen halide under the reaction conditions, the reaction is carried out with a volume ratio of nitrite:CO=0.1–10:1, a pressure from 0.5 to 10 bar and a temperature from 50 to −150° C. being used and hydrogen halide is added stepwise or continuously.

2. The process of claim 1, wherein R represents methyl or ethyl.

3. The process of claim 2, wherein R represents methyl.

4. The process of claim 1, wherein the volume ratio of nitrite:CO is 0.2–4:1.

5. The process of claim 4, wherein the volume ratio of nitrite:CO is 0.3–3:1.

6. The process of claim 1, wherein a pressure from 0.8 to 7 bar is used.

7. The process of claim 6, wherein a pressure from 1 to 6 bar is used.

8. The process of claim 1, wherein a temperature from 70° to 120° C. is used.

9. The process of claim 8, wherein a temperature from 70° to 110° C. is used.

10. The process of claim 1, wherein the support used is an acid metal phosphate, acid metal monohydrogen phosphate or acid metal dihydrogen phosphate of an element of Group IIA, IIIA, IIIB, IV B or VB of the Periodic Table of the Elements (Mendeleev), of a rare-earth metal of atomic numbers 58–71 or of the actinides of atomic numbers 89–92 or a mixture of a plurality thereof.

11. The process of claim 10, wherein the metal phosphate, metal monohydrogen phosphate or metal dihydrogen phosphate used is selected from the group consisting of magnesium, calcium, strontium, barium, titanium, zirconium, hafnium, vanadium, niobium, tantalum, boron, aluminum, gallium, indium, lanthanum, cerium, praseodymium, neodymium, samarium, europium, gadolinium, terbium, disprosium, holmium, erbium, thulium, ytterbium, lutetium and uranium, as chemically uniform pure substances or as mixtures.

12. The process of claim 11, wherein a phosphate, hydrogen phosphate or dihydrogen phosphate or aluminium, vanadium, niobium, yttrium, lanthanum or of the rare-earth metals having automatic numbers of 58–71 or a mixture of a plurality thereof is used.

13. The process of claim 1, wherein a compound of iron, copper, bismuth, cobalt, nickel, tin, molybdenum, tungsten or of alkali or alkaline earth metals or a mixture of a plurality thereof is added to the catalyst.

14. The process of claim 1, wherein the platinum metal(s) used is/are one or more selected from the group consisting of palladium, platinum, iridium, ruthenium and rhodium.

15. The process of claim 1, wherein the platinum metal halide(s) used is/are one or more selected from the group consisting of simple or complex fluorides, chlorides, bromides and iodides.

16. The process of claim 15, wherein the platinum metal halide is one from the group consisting of chlorides and bromides.

17. The process of claim 1, wherein the reaction is carried out in the presence of an inert gas, the inert gas comprising from 20 to 80% by volume of the total gas volume.

18. The process of claim 1, wherein the reaction is carried out at a space velocity over the catalyst from 700 to 5000 l of the mixture of the gaseous reactants per hour per l of catalyst.

19. The process of claim 1, wherein in the active state the catalyst contains from 0.01 to 8% by weight of a platinum metal halide or of a complex containing a platinum metal halide, calculated as platinum metal and based on the total weight of the catalyst.

20. The process of claim 19, wherein the catalyst contains from 0.05–4% by weight of a platinum metal halide or of a complex containing a platinum metal halide, calculated as platinum metal and based on the total weight of the catalyst.

* * * * *